United States Patent
Mucilli et al.

(10) Patent No.: US 11,376,067 B2
(45) Date of Patent: *Jul. 5, 2022

(54) CONNECTOR ASSEMBLY FOR AN ELECTROSURGICAL SYSTEM

(71) Applicant: Covidien LP, Mansfield, MA (US)

(72) Inventors: Jason M. Mucilli, Lakewood, CO (US); James H. Orszulak, Nederland, CO (US)

(73) Assignee: COVIDIEN LP, Mansfield, MA (US)

(*) Notice: Subject to any disclaimer, the term of this patent is extended or adjusted under 35 U.S.C. 154(b) by 1017 days.

This patent is subject to a terminal disclaimer.

(21) Appl. No.: 16/042,113

(22) Filed: Jul. 23, 2018

(65) Prior Publication Data

US 2018/0325591 A1 Nov. 15, 2018

Related U.S. Application Data

(63) Continuation of application No. 13/903,382, filed on May 28, 2013, now Pat. No. 10,028,786.

(Continued)

(51) Int. Cl.
*A61B 18/18* (2006.01)
*A61B 18/14* (2006.01)
(Continued)

(52) U.S. Cl.
CPC .............. *A61B 18/18* (2013.01); *A61B 18/14* (2013.01); *A61B 18/1445* (2013.01);
(Continued)

(58) Field of Classification Search
CPC ..... A61B 18/14; A61B 18/1445; A61B 18/18; A61B 2018/00178
See application file for complete search history.

(56) References Cited

U.S. PATENT DOCUMENTS 3,760,812 A 9/1973 Timm et al.
3,895,635 A 7/1975 Justus et al.
(Continued)

FOREIGN PATENT DOCUMENTS

EP 0061246 A1 9/1982
EP 0750886 A1 1/1997
(Continued)

OTHER PUBLICATIONS

Chinese Office Action from Appl. No. 201310267913.5 dated Sep. 12, 2016.
(Continued)

*Primary Examiner* — Michael F Peffley
*Assistant Examiner* — Amanda L Zink
(74) *Attorney, Agent, or Firm* — Carter, DeLuca & Farrell LLP

(57) ABSTRACT

A connector assembly is provided. The connector assembly includes a housing having a first end that includes one or more mechanical interfaces thereon. The at least one mechanical interface configured to selectively engage a corresponding mechanical interface on an electrosurgical generator. A second end is configured to selectively engage an end of an electrosurgical cable to couple the electrosurgical generator to an electrosurgical instrument. A plurality of splines extends along an interior of the housing and is configured for electrical communication with a plurality of corresponding electrical conductors of the electrosurgical cable.

20 Claims, 5 Drawing Sheets

Related U.S. Application Data

(60) Provisional application No. 61/666,080, filed on Jun. 29, 2012.

(51) Int. Cl.
   *H01R 4/48*  (2006.01)
   *H01R 13/58* (2006.01)
   *A61B 18/00* (2006.01)

(52) U.S. Cl.
   CPC ......... *H01R 4/489* (2013.01); *H01R 13/5833* (2013.01); *A61B 2018/00178* (2013.01)

(56) References Cited

U.S. PATENT DOCUMENTS

| | | | |
|---|---|---|---|
| 4,413,304 | A | 11/1983 | Gerry |
| 5,058,172 | A | 10/1991 | Ross |
| 5,693,045 | A | 12/1997 | Eggers |
| 5,813,404 | A | 9/1998 | Devlin |
| 5,831,210 | A | 11/1998 | Nugent |
| 6,113,596 | A | 9/2000 | Hooven et al. |
| 6,190,385 | B1 | 2/2001 | Tom et al. |
| 6,300,573 | B1 | 10/2001 | Horie et al. |
| 6,394,949 | B1 | 5/2002 | Crowley et al. |
| 7,057,111 | B2 | 6/2006 | Fung et al. |
| 7,090,673 | B2 | 8/2006 | Dycus et al. |
| 7,147,638 | B2 | 12/2006 | Chapman et al. |
| 7,156,846 | B2 | 1/2007 | Dycus et al. |
| 7,497,826 | B2 | 3/2009 | Ouchi |
| 8,435,079 | B1 * | 5/2013 | Osa .......... A61B 5/30 600/378 |
| 8,439,714 | B2 * | 5/2013 | Putz .......... H01R 4/5008 600/372 |
| 10,028,786 | B2 | 7/2018 | Mucilli et al. |
| 2001/0039412 | A1 | 11/2001 | Fariabi |
| 2002/0095079 | A1 * | 7/2002 | Putz .......... A61N 1/05 439/909 |
| 2002/0197905 | A1 | 12/2002 | Kaufmann et al. |
| 2003/0229344 | A1 | 12/2003 | Dycus et al. |
| 2004/0204679 | A1 | 10/2004 | Visconti et al. |
| 2006/0148306 | A1 | 7/2006 | Desinger et al. |
| 2008/0071261 | A1 | 3/2008 | Orszulak |
| 2008/0171938 | A1 | 7/2008 | Masuda et al. |
| 2009/0111317 | A1 | 4/2009 | Fitzpatrick |
| 2010/0167586 | A1 | 7/2010 | Vayrynen |
| 2019/0109397 | A1 * | 4/2019 | Sugiura .......... H01R 13/03 |

FOREIGN PATENT DOCUMENTS

| | | |
|---|---|---|
| EP | 1201188 A1 | 5/2002 |
| EP | 1902681 A1 | 3/2008 |
| GB | 2321193 A | 7/1998 |
| GB | 2326519 A | 12/1998 |
| WO | 02071965 A1 | 9/2002 |
| WO | 2006048199 A1 | 5/2006 |
| WO | 2006081191 A1 | 8/2006 |
| WO | 2008059248 A1 | 5/2008 |
| WO | 2008119884 A1 | 10/2008 |
| WO | 2010065120 A1 | 6/2010 |

OTHER PUBLICATIONS

Extended European Search Report corresponding to EP 13 17 3537.5, completed Oct. 30, 2013 and dated Nov. 7, 2013; (7 pp).
Extended European Search Report issued in corresponding Appl. No. EP 19163816.2 dated Jul. 15, 2019 (8 pages).

* cited by examiner

CONNECTOR ASSEMBLY FOR AN ELECTROSURGICAL SYSTEM

CROSS-REFERENCE TO RELATED APPLICATIONS

This application is a continuation of U.S. patent application Ser. No. 13/903,382 filed on May 28, 2013, now U.S. Pat. No. 10,028,786.

BACKGROUND

Technical Field

The present disclosure relates to a connector assembly configured for use with electrosurgical systems that utilize electrosurgical cables configured to couple an electrosurgical instrument to a source of electrosurgical energy. More particularly, the present disclosure relates to a connector assembly configured for use with electrosurgical cables that utilize a double helix wound electrical connector configuration.

Description of Related Art

Electrosurgery involves application of high radio frequency current to a surgical site to cut, ablate, seal, coagulate or desiccate tissue. An electrosurgical generator, typically, delivers radio frequency energy to one or more active electrodes of an electrosurgical instrument. The electrosurgical instrument may be configured to function in various modalities, e.g., bipolar or monopolar modes.

Various types of electrosurgical cables may be utilized to transmit the electrosurgical energy from the electrosurgical generator to the electrosurgical instrument. Due to the radiative nature of RF energy, stray electrosurgical RF energy is emitted outside the transmission path of certain types of electrosurgical cables, which may reduce treatment energy. Moreover, electrical fields associated with the stray electrosurgical RF energy may interfere with the operation of other electronic equipment in the operational theatre, e.g., patient monitoring equipment in the surgical environment.

In order to overcome the aforementioned shortcomings associated with certain types of electrosurgical cables, electrosurgical cables have been developed which utilize a double helix wound electrical connector configuration. Present day connector assemblies, however, currently provide connection solutions for IDC ribbon cables, solder-cup D-subminiature cables, crimp style plastic connectors and surface mount PCB connectors (e.g., right and straight angle PCB connectors) and are not, typically, suitable for use with electrosurgical cables that utilize double helix wound electrical connector configuration. That is, the integrity of the double helix configuration of an electrosurgical cable is compromised when these types of connectors are utilized to connect the electrosurgical cable to the electrosurgical generator and/or electrosurgical instrument.

SUMMARY

In view of the foregoing, a connector assembly configured for use with electrosurgical cables that utilize a double helix wound electrical connector configuration may prove advantageous in the medical arts.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides a connector assembly. The connector assembly includes a housing having a first end including one or more mechanical interfaces thereon. The mechanical interface(s) is configured to selectively engage a corresponding mechanical interface on an electrosurgical generator or electrosurgical instrument. The mechanical interface at the first end of the housing may be a keying tract that is configured to selectively engage a keying structure on the electrosurgical generator or the electrosurgical instrument. A second end of the housing is configured to selectively engage an end of an electrosurgical cable that is configured to couple the electrosurgical generator to the electrosurgical instrument. The second end of the housing may be permanently coupled or detachable to the electrosurgical cable. A plurality of splines extend along an interior of the housing and are configured for electrical communication with a corresponding plurality of electrical conductors of the electrosurgical cable.

The plurality of electrical conductors may include supply and return lines that are wound in a double helix around a dielectric insulator within the electrosurgical cable. The plurality of splines may include two or more splines that extend along an inner peripheral wall within the housing in a double helical arrangement. Each spline may include one or more biasing members thereon that are configured to both align the plurality of splines with the corresponding plurality of electrical conductors of the electrosurgical cable and facilitate coupling the connector assembly to the electrosurgical cable. The biasing member(s) may include a plurality of electrically conductive spring-loaded balls.

The electrosurgical generator may be configured to provide radio frequency energy to the electrosurgical instrument to coagulate, cut, seal or ablate tissue. The electrosurgical generator and the electrosurgical instrument may be operable in bipolar or monopolar modalities of operation.

An aspect of the present disclosure provides a system for performing an electrosurgical procedure. The system includes an electrosurgical generator and an electrosurgical cable. The system includes a connector assembly including a housing having a first end including one or more mechanical interfaces thereon. The mechanical interface(s) is configured to selectively engage a corresponding mechanical interface on an electrosurgical generator or electrosurgical instrument. The mechanical interface at the first end of the housing may be a keying tract that is configured to selectively engage a keying structure on the electrosurgical generator or the electrosurgical instrument. A second end of the housing is configured to selectively engage an end of an electrosurgical cable that is configured to couple the electrosurgical generator to the electrosurgical instrument. The second end of the housing may be permanently coupled or detachable to the electrosurgical cable. A plurality of splines extend along an interior of the housing and are configured for electrical communication with a corresponding plurality of electrical conductors of the electrosurgical cable.

The plurality of electrical conductors may include supply and return lines that are wound in a double helix around a dielectric insulator within the electrosurgical cable. The plurality of splines may include two or more splines that extend along an inner peripheral wall within the housing in a double helical arrangement. Each spline may include one or more biasing members thereon that are configured to both align the plurality of splines with the corresponding plurality of electrical conductors of the electrosurgical cable and facilitate coupling the connector assembly to the electrosurgical cable. The biasing member(s) may include a plurality of electrically conductive spring-loaded balls.

The electrosurgical generator may be configured to provide radio frequency energy to the electrosurgical instrument to coagulate, cut, seal or ablate tissue. The electrosurgical generator and the electrosurgical instrument may be operable in bipolar or monopolar modalities of operation.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In accordance with the instant disclosure, a connector assembly configured for use with electrosurgical cables that utilize a helical configuration is provided. The connector assembly is configured to interchangeably couple to an electrosurgical cable for coupling the electrosurgical cable to an electrosurgical energy source and/or one or more types of electrosurgical instruments.

Figure 1:
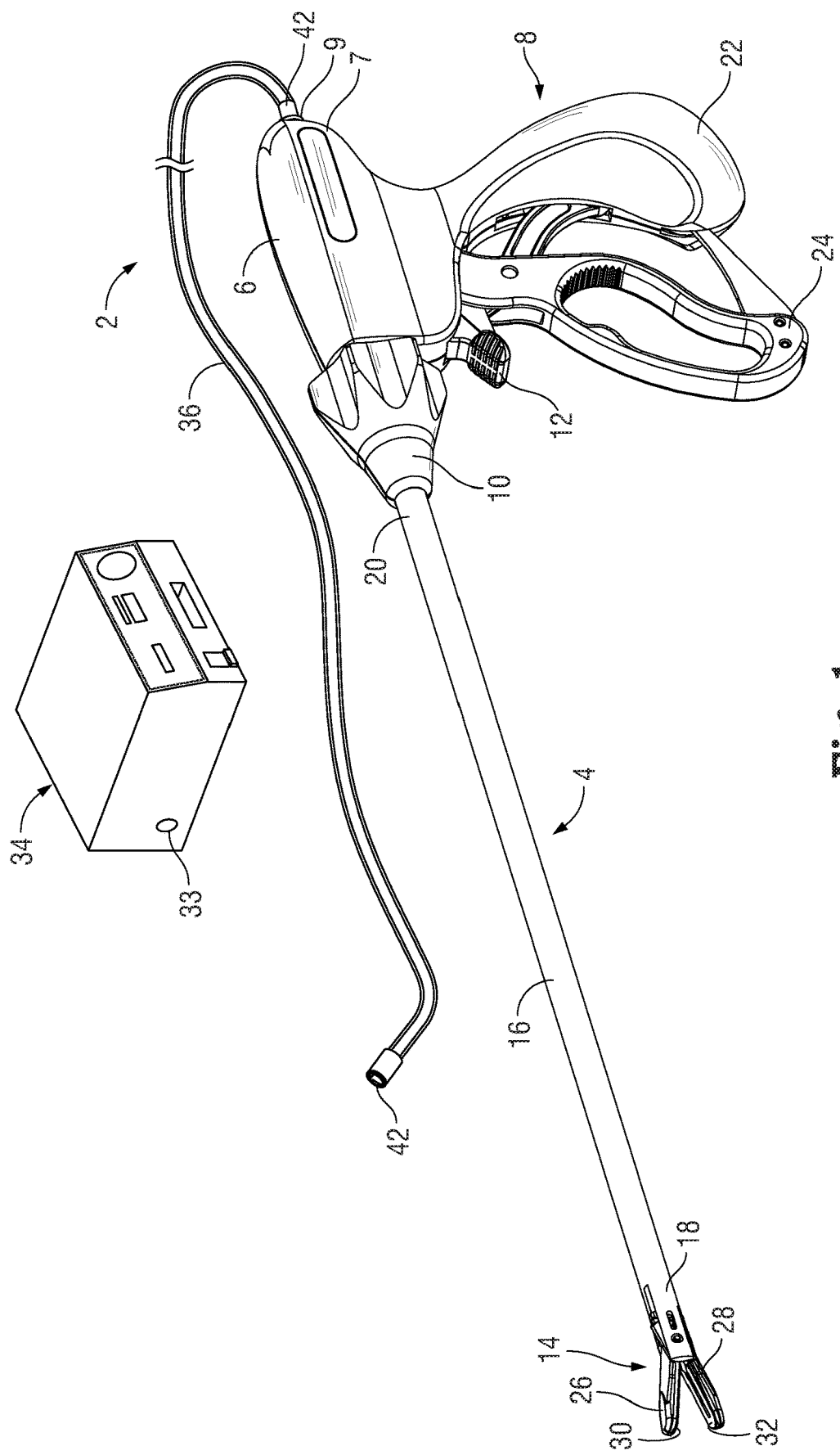
FIG. 1 is a perspective view of a bipolar electrosurgical system configured for use with a connector assembly according to an embodiment of the instant disclosure.

FIG. 1 shows an electrosurgical system 2 according to the present disclosure. The system 2 is a bipolar electrosurgical system that includes an electrosurgical forceps 4. Forceps 4 generally includes a housing 6, a shaft 16 a handle assembly 8, a rotating assembly 10 and a trigger assembly 12, which mutually cooperate with an end effector assembly 14 to grasp and treat tissue. Shaft 16 includes a distal end 18 that mechanically engages end effector assembly 14 and a proximal end 20 that mechanically engages housing 6 proximate the rotating assembly 10. Handle assembly 8 includes a fixed handle 22 and a movable handle 24. End effector assembly 14 includes jaw members 26, 28 movable from a first position wherein the jaw members 26, 28 are spaced relative to one another to a closed position wherein the jaw members 26 and 28 cooperate to grasp tissue therebetween. Each of the jaw members 26, 28 includes an electrically conductive sealing plate 30, 32 connected to an energy source (e.g., a generator 34) that communicates electrosurgical energy through tissue held between jaw members 26, 28. Electrosurgical RF energy is supplied to the forceps 4 by generator 34 via an electrosurgical cable 36 having a supply line 38 operatively connected to an active electrode (not explicitly shown) and returned through the return line 40 operatively connected to the return electrode (not explicitly shown). Cable 36 couples to a proximal end 7 of a housing 6 via a connector assembly 42 that couples to cable 36. In particular, one or more mechanical interfaces (e.g., keying structure 9, threads, or the like) are provided at proximal end 7 and are configured to selectively engage one or more corresponding mechanical interfaces on connector assembly 42, described in greater detail below.

Figure 2:
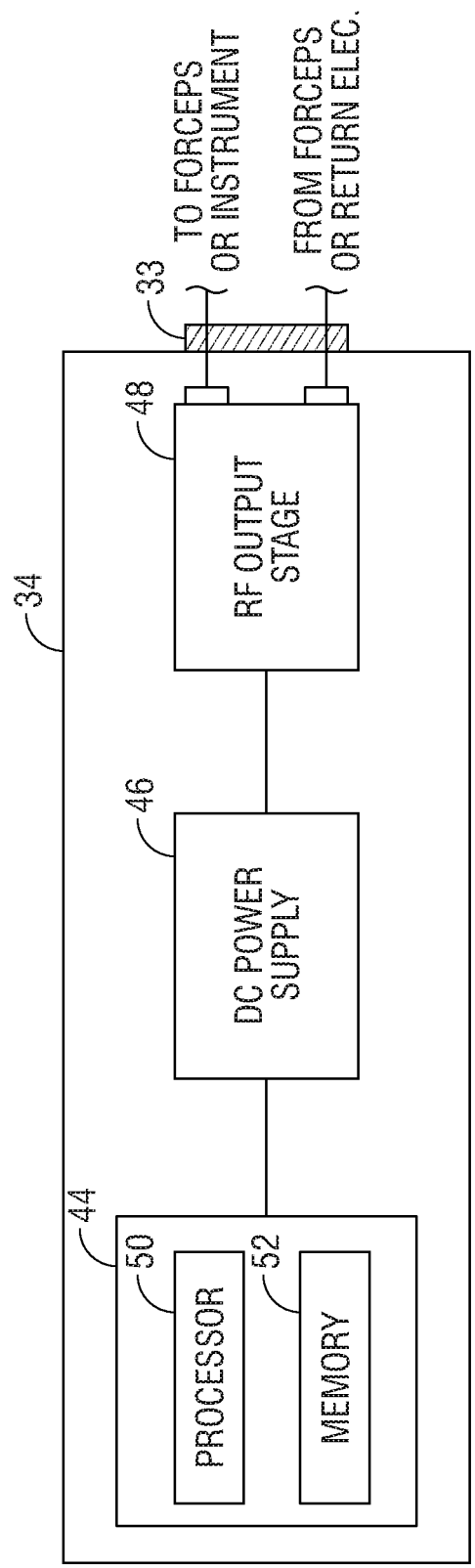
FIG. 2 is a schematic block diagram of a generator depicted in FIG. 1.

FIG. 2 shows a schematic block diagram of generator 34. Briefly, generator 34 includes a controller 44, a high voltage power supply 46 ("HVPS 46") and an RF output stage 48. HVPS 46 provides DC power to the RF output stage 48, which then converts DC power into RF energy and delivers the RF energy to forceps 4 to electrosurgically treat tissue, e.g., coagulate, cut, seal or ablate tissue. Controller 44 includes a microprocessor 50 operatively connected to a memory 52 which may be volatile type memory (e.g., RAM) and/or non-volatile type memory (e.g., flash media, disk media, etc.).

One or more mechanical interfaces (e.g., a keying structure 33, threads, or the like) are provided on an outside of the generator 34 and are configured to selectively couple to connector assembly 42 (FIGS. 1-2). In the illustrated embodiment, keying structure 33 is provided on an outside of electrosurgical generator 34 and is configured to selectively engage a corresponding keying tract 43 (FIG. 4) on connector assembly 42, described in more detail below. Alternatively, or in addition thereto, the mechanical interface(s) on generator 34 may be in the form of or may include a plurality of threads (not explicitly shown) that are configured to engage a corresponding plurality of threads 45 on connector assembly 42, see FIG. 4 for example.

Figure 3:
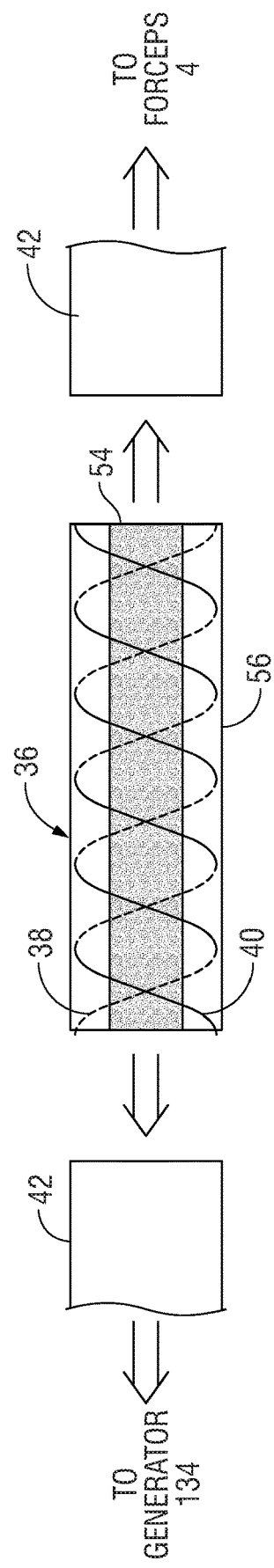
FIG. 3 is a cross-sectional view of a helical electrosurgical cable depicted in FIG. 1 configured for use with the connector assembly.

FIG. 3 shows a cross-sectional view of cable 36. Cable 36 includes a plurality of electrical conductors in the form of supply and return lines 38, 40. Supply and return lines 38, 40 may be peripherally insulated via one or more suitable types of insulating materials, e.g., a removable plastic sheathing (not explicitly shown). In accordance with the instant disclosure, supply and return lines 38, 40 are helix wound and may be of any length depending on geometric configuration and physical properties (e.g., tensile strength, flexibility, etc.) of materials used in manufacturing of cable components. Supply and return lines 38, 40 are oriented in a double helix that includes two congruent helixes with the same axis, differing by an angular translation of at least but not limited to 180 degrees along the axis. Supply and return lines 38, 40 may be oriented in a plurality of other arrangements which wrap the lines 38, 40 around themselves. The arrangement of the lines 38, 40 in this double helix configuration orients the opposing electrical fields generated by the electrosurgical RF energy passing therethrough to mitigate and/or cancel out thereby minimizing the amount of stray electrical RF energy. Supply and return lines 38, 40 are wound within the cable 36 around a dielectric insulator 54, which provides support for the supply and return lines 38, 40 and an insulative sheath 56 that covers supply and return lines 38, 40. Insulator 54 and the sheath 56 may be formed from the same type of material. In the illustrated embodiment, sheath 56 may be pulled back (or a portion thereof may be removable) to expose supply and return lines 38, 40 to facilitate coupling cable 36 to connector assembly 42. Likewise, the sheathing that covers supply and return lines 38, 40 may be configured to be pulled back or removed.

In accordance with the instant disclosure, cable 36 provides a transmission medium to deliver RF energy from generator 34 to a tissue site. Cable 36 orients supply and return lines 38, 40 so that the electrical fields generated therethrough are canceled, thereby reducing the amount of leaked stray RF energy. More specifically, placement and the physical geometric orientation of supply and return lines 38, 40 in the double helix configuration provides for reduced RF leakage by the electrical field coupling generated during transmission of electrosurgical RF energy and maximizes the amount of energy delivered to the treatment site. Other positive attributes associated with placement and orientation of supply and return lines 38, 40 in the double helix configuration may include, but are not limited to: increased safety in the operating theatre due to reduced stray energy; decreased capacitive and RF field leakage, which, in turn may improve RF control of the delivered energy; decreased RF transmission loss, which, in turn, may improve efficiency of the generator 36; and decreased RF noise to additional equipment found in (or adjacent) the surgical theatre, such as patient monitoring equipment.

Figure 4:
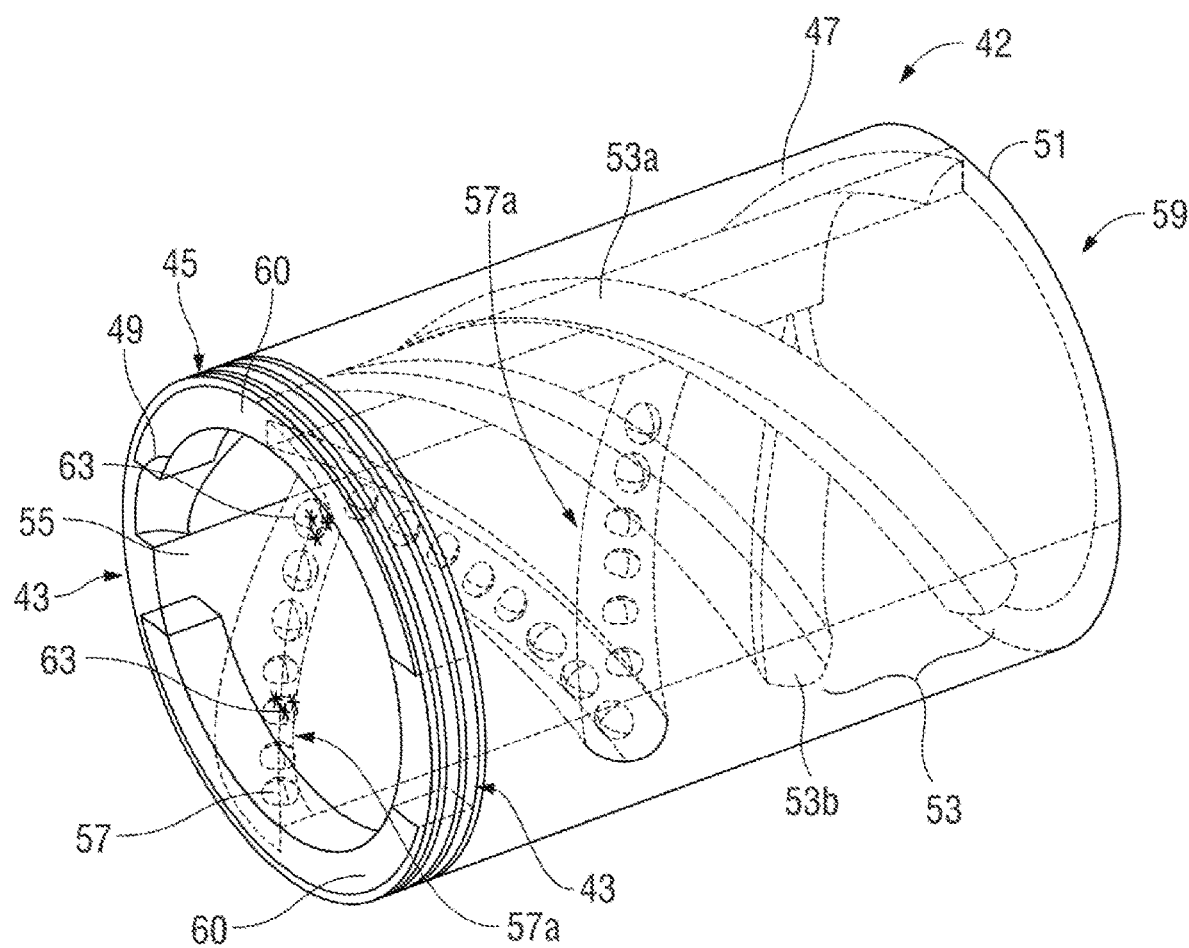
FIG. 4 is a right perspective view of the helical connector assembly.

With reference to FIG. 4, connector assembly 42 is illustrated. Connector assembly 42 may be made from any suitable material including, but not limited to plastic, ceramic, metal, etc. In the illustrated embodiment, connector assembly 42 is made from a relatively rigid plastic.

Continuing with reference to FIG. 4, connector assembly 42 includes a housing 47 having a first end 49 and a second end 51. First end 49 includes one or more mechanical interfaces disposed thereon, e.g., keying tract 43 and/or threads 45. As noted above, the keying tract 43 is configured to selectively engage keying structure 33 on the generator 34 and/or forceps 4.

Second end 51 is configured to selectively engage an end of cable 36. Specifically, second end 51 includes an opening 59 of suitable configuration configured to receive a portion of cable 36 therein after sheath 56 has been sufficiently pulled back (or removed). A friction-fit or press-fit may be utilized to securely join cable 36 with connector assembly 42.

A plurality of splines 53 extend along an interior wall 55 of the housing 47 and are configured for electrical communication with supply and return lines 38, 40 of electrosurgical cable 36. In the illustrated embodiment, the plurality of splines 53 are shown including two splines 53a, 53b that extend along interior wall 55 within housing 47 and in a double helical configuration similar to that of supply and return 38, 40 in cable 36. In one particular embodiment, supply line 38 is configured for electrical communication with spline 53a and return line 40 is configured for electrical communication with spline 53b; other electrical configurations are contemplated.

In embodiments, each spline 53a, 53b of the plurality splines 53 includes one or more biasing members 57 that are configured to align the splines 53a, 53b with supply and return lines 38, 40 of cable 36 and to facilitate coupling connector assembly 42 to cable 36. In the illustrated embodiment, biasing members 57 include a plurality of electrically conductive spring loaded balls 57a that follow the same general path of splines 53a, 53b. Spring loaded balls 57a are urged radially outward and are configured to press against supply and return lines 38, 40 when cable 36 is inserted into connector assembly 42. This pressing against supply and return lines 38, 40 facilitates maintaining cable 36 and connector assembly 42 in a secured electrical engagement with one another.

Spring loaded balls 57a may be made from any suitable metallic material including, but not limited to copper, brass, nickel, gold etc., capable of making good RF energy contact to cable 36, etc. In the illustrated embodiment, spring loaded balls 57a are formed from a conductive material, e.g., metal, which is configured to increase electrical continuity between splines 53a, 53b and supply and return lines 38, 40.

In one embodiment, a portion of sheathing 56 may be pulled back (or removed) to expose supply and return lines 38, 40. Thereafter, the insulator covering supply and return lines 38, 40 may be removed and the exposed portion of cable 36 may be inserted into connector assembly 42. Spring loaded balls 57a press against supply and return lines 38, 40 to secure cable 36 to connector assembly 42 and maintain supply and return lines 38, 40 in electrical communication with splines 53a, 53b. Subsequently, keying tract 43 may be utilized to couple connector assembly 42 to generator 34 or forceps 4.

The unique configuration of connector assembly 42 allows a user to couple cable 36 to generator 34 and/or forceps 4 while maintaining the double helix configuration of cable 36 thus, overcoming the aforementioned drawbacks associated with present day connectors.

From the foregoing and with reference to the various figure drawings, those skilled in the art will appreciate that certain modifications can also be made to the present disclosure without departing from the scope of the same. For example, those skilled in the art will understand that the connector assembly 42 may be adapted for use with either an endoscopic instrument (as shown in FIG. 2) or an open instrument (not shown).

In embodiments, one or more structures (or mechanisms) may be utilized to pierce the sheathing that covers supply and return lines 38, 40 when cable 36 is inserted into connector assembly 42. For example, in one embodiment, all spring loaded balls 57a could include a connective cutter blade 63 (or the like), that is configured to simultaneously pierce the sheathing and make good RF contact to the supply and return lines 38, 40 (FIG. 4). In this instance, a user does not have to pull back or remove the sheathing that covers supply and return lines 38, 40 in order to obtain an electrical connection between supply and return lines 38, 40 and splines 53a, 53b, respectively.

In embodiments, connector assembly 42 may be permanently coupled to forceps 4, generator 34 or cable 36. The specific fixation configurations of connector assembly 42 to forceps 4, generator 34 or cable 36 may depend on a manufacturer's preference, a specific surgical procedure, an end user's contemplated needs, etc.

In embodiments, a proximal face 60 of connector assembly 42 adjacent keying tract 42 may be conductive and in electrical communication with splines 53a, 53b to provide an uninterrupted path for current flow.

Figure 5:
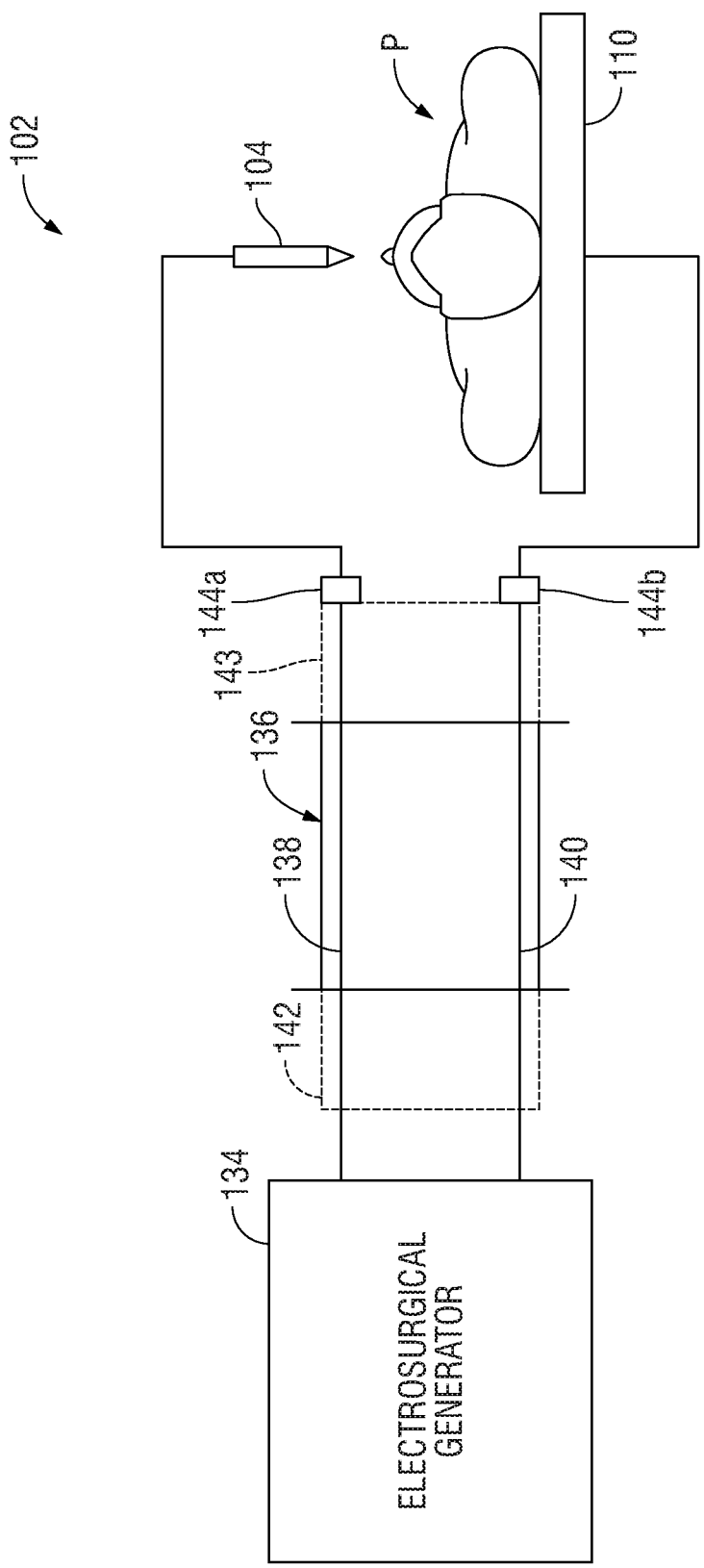
FIG. 5 is a schematic block diagram of a monopolar electrosurgical system configured for use with the connector assembly.

In embodiments, connector assembly may be configured to selectively couple to a forceps 104 that is configured for monopolar operation. FIG. 5 is a schematic illustration of another electrosurgical system 102 according to the present disclosure. System 102 is a monopolar electrosurgical system that includes an electrosurgical instrument 104 having one or more electrodes for treating tissue of a patient P. Electrosurgical RF energy is supplied to the instrument 104 by generator 134 via a supply line 138. Energy is returned to generator 134 through a return electrode 110 and transmitted through return line 140. Supply and return lines 138, 140 are enclosed within cable 136. Connector assembly 142 may be utilized to couple generator 134 to cable 136. Unlike connector assembly 142, however, connector assembly 143 includes two (2) ports (or hubs) 144a, 144b. Port 144a is configured to selectively (or permanently) couple to forceps 104 and port 144b is configured to selectively couple to return electrode 110. Other than ports 144a, 144b, connector assembly 142 is configured to function identically to connector assembly 42.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A electrosurgical system, comprising:
   an electrosurgical energy source;
   a connector assembly configured to couple an electrosurgical instrument to the electrosurgical energy source; and
   a spring-loaded ball disposed within the connector assembly and having a cutter element configured to pierce an electrosurgical cable received within the connector assembly to electrically couple the electrosurgical instrument to the electrosurgical energy source via the electrosurgical cable.

2. The electrosurgical system according to claim 1, wherein the connector assembly includes a keying tract configured to couple the connector assembly to the electrosurgical energy source.

3. The electrosurgical system according to claim 1, further comprising an electrically conductive spline disposed within the connector assembly.

4. The electrosurgical system according to claim 3, wherein the electrically conductive spline is helically wound about the connector assembly.

5. The electrosurgical system according to claim 1, wherein the electrosurgical energy source is a radiofrequency energy generator.

6. The electrosurgical system according to claim 1, wherein the spring-loaded ball is electrically conductive.

7. The electrosurgical system according to claim 1, wherein the spring-loaded ball is configured to bias the electrosurgical cable to maintain the electrosurgical cable within the connector assembly.

8. The electrosurgical system according to claim 1, wherein the connector assembly includes a first hub configured to electrically couple to a supply line of the electrosurgical cable and a second hub configured to electrically couple to a return line of the electrosurgical cable.

9. The electrosurgical system according to claim 1, wherein the cutter element includes a blade extending from the spring-loaded ball configured to pierce the electrosurgical cable.

10. A electrosurgical system, comprising:
    an electrosurgical energy source;
    a connector assembly configured to couple an electrosurgical instrument to the electrosurgical energy source; and
    a spring-loaded ball disposed within the connector assembly and configured to engage an electrosurgical cable received within the connector assembly to couple the electrosurgical instrument to the electrosurgical energy source via the electrosurgical cable.

11. The electrosurgical system according to claim 10, further comprising a cutter element disposed within the connector assembly and configured to pierce the electrosurgical cable.

12. The electrosurgical system according to claim 11, wherein the cutter element extends from the spring-loaded ball.

13. The electrosurgical system according to claim 10, wherein the connector assembly includes a keying tract configured to couple the connector assembly to the electrosurgical energy source.

14. The electrosurgical system according to claim 10, wherein the connector assembly includes a helically wound electrically conductive spline.

15. The electrosurgical system according to claim 10, wherein the spring-loaded ball is electrically conductive.

16. The electrosurgical system according to claim 10, wherein the spring-loaded ball is configured to bias the electrosurgical cable to maintain the electrosurgical cable within the connector assembly.

17. The electrosurgical system according to claim 10, wherein the connector assembly includes a first hub configured to electrically couple to a supply line of the electrosurgical cable and a second hub configured to electrically couple to a return line of the electrosurgical cable.

18. A electrosurgical system, comprising:
    an electrosurgical energy source;
    an electrosurgical instrument configured to couple to the electrosurgical energy source for treating tissue;
    a connector assembly configured to couple the electrosurgical instrument to the electrosurgical energy source via an electrosurgical cable; and
    a biasing member disposed within the connector assembly and configured to bias the electrosurgical cable to maintain the electrosurgical cable within the connector assembly; and
    an electrically conductive element extending from the biasing member and configured to electrically couple the electrosurgical instrument to the electrosurgical energy source via the electrosurgical cable.

19. The electrosurgical system according to claim 18, wherein the biasing member includes a spring-loaded ball.

20. The electrosurgical system according to claim 18, wherein the electrically conductive element includes a blade configured to pierce the electrosurgical cable.

\* \* \* \* \*